US008414888B2

(12) United States Patent
Fehlings et al.

(10) Patent No.: US 8,414,888 B2
(45) Date of Patent: Apr. 9, 2013

(54) THERAPEUTIC USE OF IGG AS A NEUROPROTECTIVE AGENT

(75) Inventors: Michael Fehlings, Toronto (CA); Sherri Robins, Barrie (CA)

(73) Assignee: University Health Network, Toronto, Ontario (CA)

(*) Notice: Subject to any disclaimer, the term of this patent is extended or adjusted under 35 U.S.C. 154(b) by 573 days.

(21) Appl. No.: 12/614,252

(22) Filed: Nov. 6, 2009

(65) Prior Publication Data
US 2010/0178289 A1 Jul. 15, 2010

Related U.S. Application Data

(60) Provisional application No. 61/112,177, filed on Nov. 6, 2008.

(30) Foreign Application Priority Data

Nov. 6, 2008 (CA) .................................. 2643496

(51) Int. Cl.
*A61K 39/395* (2006.01)
(52) U.S. Cl. .................................. 424/130.1; 514/17.7
(58) Field of Classification Search .................. None
See application file for complete search history.

(56) References Cited

U.S. PATENT DOCUMENTS
6,432,404 B1 8/2002 Gallatin et al.

FOREIGN PATENT DOCUMENTS
WO 00/64473 11/2000

OTHER PUBLICATIONS

Jackowski, British Journal of Neurosurgery 9: 303-317 (1995).*
Christopher and Dana Reeve Foundation.Prevalence of Paralysis. Jul. 2009 Cited. Available at: http://www.christopherreeve.org/site/c.mtKZKgMWKwG/b.5184189/k.5587/Paralysis_Facts_Figures.htm.
Spinal Cord Injury Information Network. Spinal Cord Injury Facts and Figures at a Glance 2009. Jul. 2009 cited. Available at: http://www.spinalcord.uab.edu/show.asp?durki=119513&site=4716&return=19775.
Blight, A. "Delayed demyelination, macrophage invasion: a candidate for "secondary" cell damage in spinal cord injury", Cent Nerv Syst Trauma, 1985. 2: p. 299-315.
Tator et al, "Review of the secondary injury theory of acute spinal cord trauma with emphasis on vascular mechanisms", J. Neurosurg., 1991. 75: p. 15-26.
Kwon et al, "Pathophysiology and pharmacologic treatment of acute spinal cord injury", Spine J., 2004. 4: p. 451-64.
Profyris et al, "Degenerative and regenerative mechanisms governing spinal cord injury", Neurobiology of Disease, 2004. 15: p. 415-436.
Fleming et al, "The cellular inflammatory response in human spinal cords after injury", Brain, 2006. 129: p. 3249-3269.
Hausmann, O., "Post-traumatic inflammation following spinal cord injury", Spinal Cord, 2003. 41: p. 369-378.

Popovich et al, "The cellular inflammatory response after spinal cord injury in Sprague-Dawley and Lewis rats", J. Comp. Neurol., 1997. 377 p. 443-464.
Sroga et al, "Rats and mice exhibit distinct inflammatory reactions after spinal cord injury", J. Comp. Neurol., 2003. 462: p. 223-240.
Donnelly et al, "Inflammation and its role in neuroprotection, axonal regeneration and function recovery after spinal cord injury", Experimental Neurology, 2008. 209: p. 378-388.
Cassatella, M. "The production of cytokines by polymorphonuclear neutrophils", Immunol. Today, 1995. 16: p. 21-26.
Clark et al, "Inducible nitric oxide synthase expression in the cerebrovascular smooth muscle and neutrophils after traumatic brain injury in immature rats", Pediatr. Res., 1996. 39: p. 784-790.
MacMicking et al, "Nitric oxide and macrophage function", Annu. Rev. Immunol., 1997. 15: p. 323-350.
Beckman et al, "Apparent hydroxyl radical production by peroxynitrite: implications for endothelial injury from nitric oxide and superoxide", PNAS, 1990. 87: p. 1620-1624.
Horn et al, "Another barrier to regeneration in the CNS: activated macrophages induce extensive retraction of dystrophic axons through direct physical interactions", J. Neurosci., 2008. 28: p. 9330-41.
Kansas, G. "Selectins and their ligands: current concepts and controversies", Blood, 1996. 88: p. 3259-3287.
Lee et al, "Cytokine chemokine expresssion in contused rat spinal cord" Neurochem. Int., 2000b. 36: p. 417-425.
McTigue et al, "Selective chemokine mRNA accumulation in the rat spinal cord after contusion injury", J. Neurosci. Res., 1998. 53: p. 368-376.
Schnell et al, "Acute inflammatory responses to mechanical lesions in the CNS: differences between brain and spinal cord", Eur. J. Neurosci, 1999. 11: p. 3648-3658.
Young, W. "Methylprednisolone and spinal cord injury", J. Neurosurg., 2002. 96: p. 141-142.
Popovich et al, "Depletion of hematogenous macrophages promotes partial hindlimb recovery and neuroanatomical repair after experimental spinal cord injury", Experimental Neurology, 1999. 158: p. 351-365.
Noble et al, "Matrix metalloproteinases limit functional recovery after spinal cord injury by modulation of early vascular events", J. Neurosci., 2002. 22: p. 7526-7535.
Taoka et al, "Role of neutrophils in spinal cord injury in the rat", Neuroscience, 1997. 79: p. 1177-82.
Ditor et al, "A therapeutic time window for anti-CD 11d monoclonal antibody treatment yielding reduced secondary tissue damage and enhanced behavioral recovery following severe spinal cord injury", J. Neurosurg. Spine, 2006. 5: p. 343-352.
Gris et al, "Transient blockade of the CD11d/CD18 integrin reduces secondary damage after spinal cord injury, improving sensory, autonomic, and motor function", J. Neurosci., 2004. 24: p. 4043-4051.
Prasad et al, "Therapeutic preparations of normal polyspecific IgG (IVIg) induce apoptosis in human lymphocytes and monocytes: a novel mechanism of action of IVIg involving the Fas apoptotic pathway", J. Immunol., 161: 3781-3790, 1998.

(Continued)

*Primary Examiner* — Robert C Hayes
(74) *Attorney, Agent, or Firm* — Nixon Peabody LLP; David S. Resnick; Leena H. Karttunen Contarino

(57) ABSTRACT

The present invention relates to compositions containing IgG and methods for the promotion of nerve regeneration or prevention or inhibition of neuronal degeneration by IgG to ameliorate the effects of injury, disorder or disease of the nervous system.

6 Claims, 13 Drawing Sheets

OTHER PUBLICATIONS

Stephan von Gunten, et al, "Immunologic and functional evidence for anti-Siglec-9 autoantibodies in intravenous immunoglobulin preparations", Blood, 108: 4255-4259, 2006.

Shapiro et al, "Intravenous Gamma Globulin Inhibits the Production of Matrix Metalloperoteinase-9 in Macrophages", Cancer, 95: 2032-2037, 2002.

Basta M, et al, "F(ab)'2-mediated neutralization of C3a and C5a anaphylatoxins: a novel effector function of immunoglobulins", Nat. Med., 9: 431-438, 2003.

Marder et al, "Chemotactic responses of human peripheral blood monocytes to the complement-derived peptides C5a and C5a", Des Arg. J. Immunol., 134: 3325-3331, 1985.

Schmidt et al, "Fc receptors and their interaction with complement in autoimmunity" Immunology Letters, 100: 56-57, 2005.

Anthony et al. "Identification of a receptor required for the anti-inflammatory activity of IVIG", PNAS, 105: 19571-19578, 2008.

* cited by examiner

THERAPEUTIC USE OF IGG AS A NEUROPROTECTIVE AGENT

CROSS-REFERENCE TO RELATED APPLICATIONS

This application claims the benefit of priority as applicable under 35 U.S.C. §119(a) of co-pending Canadian Application Serial No. 2,643,496 filed Nov. 6, 2008, and also claims the benefit as applicable under 35 U.S.C. §119 (e) of United States Provisional Application Ser. No. 61/112,177, filed Nov. 6, 2008, the entire contents of which are incorporated herein by reference.

FIELD OF THE INVENTION

The present invention relates to compositions and methods for the promotion of nerve regeneration or prevention or inhibition of neuronal degeneration to ameliorate the effects of injury, disorder or disease of the nervous system.

BACKGROUND OF THE INVENTION

According to the Christopher and Dana Reeve Foundation, there are over 1.2 million people living with spinal cord injury (SCI) in the United States alone [1]. Approximately 12,000 new cases in the US are reported each year [2]. The financial burden for a person living with cervical spinal cord injury ranges from 1 to 3 million dollars over his/her lifetime. Aside from the financial burden, people with SCI and their families and caregivers also deal daily with the physical, emotional, and social effects of this devastating condition. There are few treatments currently available or even being investigated in clinical trials that address neurological impairment following traumatic SCI. Therefore, there is a dire need for effective treatments that can reduce neurological deficit and improve a patient's quality of life following SCI.

SCI consists of two defined injury processes described in terms of primary and secondary injury. The primary injury to the spinal cord involves a mechanical injury such as contusion, compression, and/or laceration of the tissue. The secondary injury, immediately following the primary injury and lasting several weeks and months, involves a cascade of cellular and molecular events that results in increased blood brain barrier (BBB) permeability, ischemia and edema, apoptosis, glutamate excitotoxicity, inflammation, demyelination, ionic imbalance, axonal degeneration, reactive gliosis, and scar formation [3-6]. Neuroinflammation, as a part of the secondary injury process, is critical in the clearance of cellular debris and promoting regeneration at the injury epicenter. However, in the acute phase, immune reactive cells (neutrophils, microglia, and macrophages) can exacerbate the initial damage by producing pro-inflammatory cytokines, reactive oxygen species, matrix-metalloproteinase (MMP), and peroxynitrite resulting in further break down of the BBB, oxidative damage to DNA and lipids, protein nitrosylation, demyelination, apoptosis, and poor functional recovery [7].

The presence of immune reactive cells early at the injury epicenter has been shown to cause a substantial amount of by-stander damage to nearby healthy tissue. Neutrophils are observed as early as 6 hrs and peak at 24 hrs after injury [8-12] while monocytes and lymphocytes are observed at the injury site 3 days after SCI. Neutrophils can further increase the extent of the inflammatory response by producing pro-inflammatory mediators such as TNF-α, IL-1, and IL-8 [13]. MMP-9 and MMP-2 produced by neutrophils, macrophages, and endothelial cells can further break down the BBB and increase leukocyte infiltration [8]. The influx of neutrophils and hematogenous macrophages is a major source of reactive oxygen species and inducible nitrous oxide synthase (iNOS) [14, 15], and these agents can cause an increase in reactive oxygen radicals and nitrous oxide (NO) at the injury epicenter. Reactive oxygen radicals can react with NO to produce peroxynitrite ($NO^-$) following injury [16]. The magnitude of the secondary damage can increase due to oxidation of proteins, DNA, and lipids by reactive oxygen radicals and peroxynitrite. In addition, activated macrophages can physically induce axonal retraction and impede axonal regeneration [17].

The recruitment of neutrophils and hematogenous macrophages to the injury epicenter occurs in a cascade-like fashion. Selectins and their counter-receptors initially mediate leukocyte rolling while integrins, I-type cellular adhesion molecule (I-CAM), V-CAM, and (PE)-CAM later mediate the tethering of leukocytes to the surface of endothelial cells [18-21]. Immune reactive cells are then activated by chemokines and chemoattractants via their respective G-protein coupled receptors. Activated immune reactive cells then extravasate into the injured tissue and produce more chemokines and pro-inflammatory cytokines to mediate the acute inflammatory response. Attenuating the inflammatory response following SCI by anti-inflammatory treatments such as high doses of methylprednisolone [22], depletion of macrophages [23], inhibition of MMP-9 [24], decreasing the availability of CAMs [25], and blocking neutrophils from entering the injury site [26, 27], has been shown to improve outcome following SCI in animals and humans.

Immunoglobulin G (IgG) isolated pooled human serum has been used clinically to treat autoimmune neuropathies such as Guillain-Barre syndrome. However, the mechanism underlying the observed benefits from IgG treatment is unclear. Many immune-modulating mechanisms for IgG have been proposed, and the exact mechanism could potentially be a combination of the following mechanisms. IgG preparations have been demonstrated to contain agonist anti-Fas antibodies, which induce monocyte and lymphocyte apoptosis via a caspase-dependent pathway [28]. IgG preparations also contain auto-antibodies toward the sialic acid-binding immunoglobulin—like lectin-9 (Siglec-9) that can induce neutrophil apoptosis via caspase-dependent pathways and pathways dependent on reactive oxygen species (ROS) [29]. In addition, IgG has been demonstrated to inhibit the production of MMP-9 in cultured macrophages via its Fc and F(ab)'$_2$ fragments [30]. IgG has also been demonstrated to bind neutrophil chemotactic factors C3a and C5a at low affinity via the constant region of the F(ab)'$_2$ fragment [31]. C5a is a potent chemotactic factor for neutrophil and macrophage recruitment and activation [32]. Recently, IgG immune-modulating mechanism is suggested to be via the regulation of Fcγ receptors expression, FcγRIIIA and FcγRIIB These receptors have low affinity to the Fc domain of the IgG molecules, and they are co-expressed on the surface of neutrophils, macrophages, mast cells, B-lymphocytes, and Natural Killer cells [33]. These Fcγ receptors work antagonistically against each other to maintain a constant balance between stimulatory and inhibitory signals in the immune system. The up-regulation of the activating FcγRIIIA receptor has been linked to immune-complex diseases and autoimmune disorders including, Arthus reaction, rheumatoid arthritis, glomerulonephritis, SLE, and ITP [33]. More specifically, sialylated N-linked glycan on the Fc fragment of IgG is required for the Fc fragment to bind to the SIGN-R1 (mice)/DC-SIGN (human) receptor on regulatory macrophages, which then up-regulate the expression of immune inhibitory FcγRIIB receptors on effector macrophages [34]. The sialic acid residue is part of a glycan, which is linked to the Fc fragment at the asparagines at position 297.

SCI is a devastating condition that can be accompanied by high levels of morbidity and mortality, while also severely reducing the quality of life of affected individuals. Current treatment options for clinicians and patients offer a low degree of efficacy and are often accompanied by undesirable complications, making the development of novel, clinically relevant therapeutic strategies a necessary goal. As mentioned above, the inflammatory response to SCI is highly complex and dynamic, contributing to both secondary injury mechanisms and wound repair pathways. It has proven difficult to target the deleterious aspects of the inflammatory response, while at the same time preserving or accentuating the beneficial elements.

Thus, there is a need for new therapeutic strategies for SCI patients.

SUMMARY OF THE INVENTION

In one aspect, there is provided a method for promoting locomotor recovery or inhibiting locomotor damage following SCI comprising the step of administering to a SCI victim an effective amount of immunoglobulin G (IgG).

In yet another aspect, there is provided a method for treating or mitigating an injury, or treating or preventing a disorder or disease of the central nervous system or peripheral nervous system comprising the step of administering an effective amount of IgG to a patient in need thereof.

In one aspect, the methods of the present invention prevent or inhibit neuronal degeneration or promote nerve regeneration.

In yet another aspect, there is provided a pharmaceutical composition comprising a pharmaceutically acceptable carrier and an effective amount of IgG for treating or mitigating an injury, or treating or preventing a disorder or disease, of the central nervous system or peripheral nervous system.

In one aspect, the pharmaceutical compositions of the present invention prevent or inhibit neuronal degeneration or promote nerve regeneration.

In yet another aspect, there is provided a pharmaceutical composition comprising a pharmaceutically acceptable carrier and an effective amount of IgG for promoting locomotor recovery or inhibiting locomotor damage following SCI.

DETAILED DESCRIPTION

Figure 1:
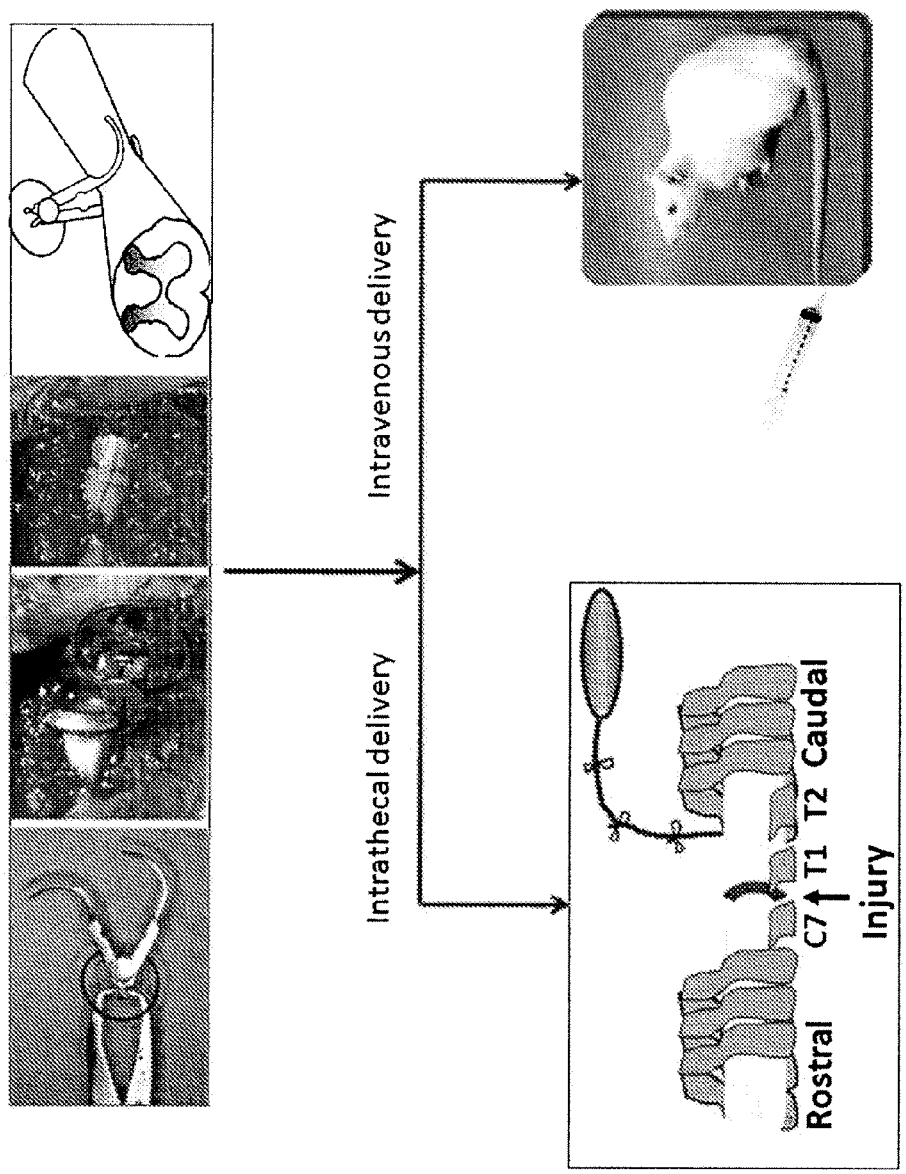
FIG. 1 illustrates the clip compression model of SCI used in the experiments, wherein female Wistar rats received a 35 g compression injury using a calibrated aneurysm clip (with 35 g of closing force) at the level of C7-T1 vertebrae. Treatment (IgG) is given either via a mini-osmotic pump and a subarachnoid catheter or intravenous injection via tail-vein

"An effective amount" means the amount of a compound that, when administered to a subject for treating or preventing a disease, is sufficient to effect such treatment or prevention for the disease. Those of skill in the art will understand that the "effective amount" may vary depending on the compound, the disease and its severity, and the age, weight, etc., of the subject to be treated. In one embodiment of the invention, the patient is a mammal. In another embodiment, the patient is a human.

The term "treatment" as used herein generally means obtaining a desired physiologic effect. The effect may be prophylactic in terms of completely or partially preventing a disease or condition or symptom thereof and/or may be therapeutic in terms of a partial or complete cure for an injury, disease or condition and/or amelioration of an adverse effect attributable to the injury, disease or condition and includes arresting the development or causing regression of a disease or condition. Treatment can also include prophylactic use to mitigate the effects of injury, should it occur. For example, in one aspect, the present invention includes pre-administration to mitigate damage prior to complex spine surgery where the spinal cord is at risk.

In one aspect, there is provided a method for promoting locomotor recovery following SCI comprising the step of administering to a SCI victim an effective amount of IgG. In one embodiment, this SCI victim is human and the IgG is IgG from pooled human serum. Suitably, this effective amount of IgG is at least partially administered within 24 hours or within 12 hours of SCI. The effective amount of IgG may be administered in a single dose or in multiple doses.

In another aspect, there is provided a method for inhibiting locomotor damage following SCI comprising the step of administering to a SCI victim an effective amount of IgG. In one embodiment, this SCI victim is human and the IgG is IgG from pooled human serum. Suitably, this effective amount of IgG is at least partially administered within 24 hours or within 12 hours of SCI. The effective amount of IgG may be administered in a single dose or in multiple doses.

In another aspect, there is provided a method for preventing or inhibiting neuronal degeneration or for promoting nerve regeneration comprising the step of administering an effective amount of IgG to a patient in need thereof. In one embodiment, this patient has suffered a SCI. In one embodiment, the patient is human and the IgG is IgG from pooled human serum. Suitably, this effective amount of IgG is at least partially administered within 24 hours or within 12 hours of SCI (before of after). The effective amount of IgG may be administered in a single dose or in multiple doses.

In yet another aspect, there is provided a method for treating or mitigating an injury, or treating or preventing a disorder or disease of the central nervous system or peripheral nervous system comprising the step of administering an effective amount of IgG to a patient in need thereof. In one embodiment, this patient has suffered a SCI. In one embodiment, the patient is human and the IgG is IgG from pooled human serum. Suitably, this effective amount of IgG is at least partially administered within 24 hours or within 12 hours of SCI (before of after). The effective amount of IgG may be administered in a single dose or in multiple doses.

In yet another aspect, there is provided a pharmaceutical composition comprising a pharmaceutically acceptable carrier and an effective amount of IgG for treating or mitigating an injury, or treating or preventing a disorder or disease of the central nervous system or peripheral nervous system. In one embodiment, the injury is a SCI. In one embodiment, the IgG is IgG from pooled human serum. The IgG may be administrable in a single dose or in multiple doses.

In yet another aspect, there is provided a pharmaceutical composition comprising a pharmaceutically acceptable carrier and an effective amount of IgG for preventing or inhibiting neuronal degeneration or for promoting nerve regeneration. In one embodiment, the IgG is IgG from pooled human serum. The IgG may be administrable in a single dose or in multiple doses.

In yet another aspect, there is provided a pharmaceutical composition comprising a pharmaceutically acceptable carrier and an effective amount of IgG for promoting locomotor recovery or inhibiting locomotor damage following SCI. In one embodiment, the IgG is IgG from pooled human serum. The IgG may be administrable in a single dose or in multiple doses.

Pharmaceutical compositions containing IgG can be administered to a patient parenterally by injection or by gradual infusion over time. For example, the composition can suitably be administered intrathecally or injected directly into the circulatory system via a vein(s) (intravenously).

The pharmaceutical compositions can be administered in any manner which enables the IgG to reach the vicinity of the injured axons to be regenerated. Preferably, the composition is injected in a pharmaceutically acceptable liquid carrier directly to the site of injury. Alternatively, an implant bearing the pharmaceutical composition may be surgically inserted. Such an implant may consist of any material which can absorb these components and slowly release it at site of implantation (eg. nitrocellulose).

As noted above, a pump may be used to deliver the IgG to the central nervous system. A variety of pumps have been designed to deliver drugs and are known to those of skill in the art. The drugs may be contained in an externally worn reservoir and delivered to the central nervous system through a small tube.

The Medtronic pump system and the Alzet osmotic mini-pump are known to deliver drugs at a controlled rate and dose over extended periods within the central nervous system.

Other means of delivery, such as through the use of polymeric microspheres, will be apparent to those skilled in this art and are intended to be comprehended within the scope of the present invention.

Pharmaceutically acceptable carriers must be compatible with both the components of the composition and the patient. Such carriers include sterile aqueous or non-aqueous solutions, suspensions, and emulsions. Examples of non-aqueous solvents include propylene glycol and other glycols, metabolizable oils such as olive oil or squalane, and injectable organic esters such as ethyl oleate. Aqueous carriers include water, alcoholic/aqueous solutions, and emulsions or suspensions (eg. saline and buffered media). Preservatives and other additives may also be present (for example, antimicrobials, anti-oxidants, chelating agents, etc.). A preferred carrier is artificial cerebrospinal fluid.

Suitable dosage ranges may be readily ascertained by those of skill in the art.

The effective amount can be delivered to the site of nerve damage in sequential doses or in a single dose. The need for a therapeutically effective temporal sequence is understood by one skilled in the art.

The effective amount of IgG may be at least partially administered within 24 hours of SCI. In various embodiments, the effective amount may be administered wholly or partially within 1, 2, 3, 4, 5, 6, 7, 8, 9, 10, 11, 12, 13, 14, 15, 16, 17, 18, 19, 20, 21, 22, 23, or 24 hours of SCI.

EXAMPLE 1

Using a moderately severe clip compression injury model in adult female Wistar rats, the objective of this study was to evaluate the inflammatory and neuroprotective effects of delayed intrathecal delivery of IgG (immunoglobulin G) following SCI.

The clip compression model of SCI was used in these experiments, with adult female Wistar rats receiving a 35 g compression injury using a calibrated aneurysm clip (with 35 g of closing force) at the level of C7-T1 vertebrae (FIG. 1).

For four of the treatment groups indicated, the animals were re-anesthetised at either 8 hours or 24 hours post-injury and a mini-osmotic pump containing either IgG (10 μg in 200 μL dispensing at 0.05 μg per hour) or BSA (bovine serum albumin) dissolved in saline was implanted under the animal's skin and a subarachnoid catheter inserted at the level of injury (FIG. 1). The fifth group received a mini-osmotic pump containing only saline and a subarachnoid catheter implantation at the time of injury. The IgG used in the studies was purified IgG from pooled human serum (5000-10000 donors), obtained from Sigma-Aldrich. Animals for Western Blot and real-time PCR analysis of immune cell infiltration and levels of inflammatory mediators were sacrificed at 7 days, while long term behavioural and neuroanatomical observations were carried out over a longer time line. BBB open field scoring, inclined plane assessment, neuropathic pain testing and FluroGold retrograde labelling of brain stem nuclei were used to evaluate the neuroprotective effects of IgG treatment.

Animals were followed for 6 weeks, with weekly behavioural and pain testing carried out. At the 7$^{th}$ week post-injury, animals were re-anesthetised and a transection of the spinal cord caudal to the injury site was carried out, where a pledget of Fluro-Gold (retrograde axonal tracer) was inserted at the caudal stump. Animals were left to recover for 8 days, at which point they were sacrificed—brains and spinal cords were collected for tissue analysis. Treatment was 0.05 µg/hour for up to 7 days.

Basso, Beattie, and Bresnahan (BBB) scores are commonly used in the evaluation of hindlimb motor function and recovery in rodent models of SCI. Here, a 21-point non-linear scale is used to assess hip, knee and ankle joints. It is important to note that the BBB scale is highly non-linear, and therefore point differences at specific places on the scale can infer different levels of biological significance.

Figure 2:
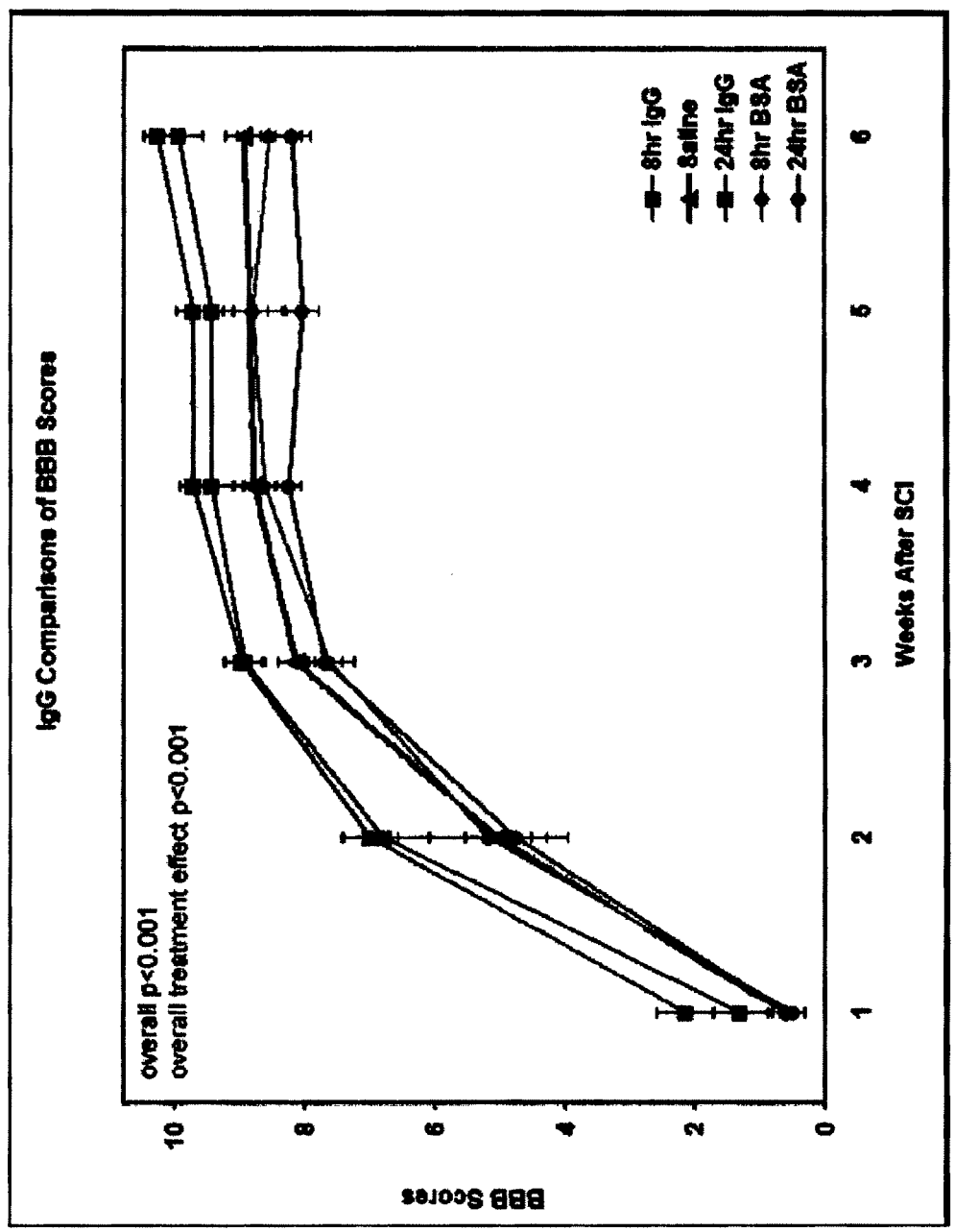
FIG. 2 illustrates hind-limb function recovery of SCI rats over 6 weeks as measured by Basso, Beattie, and Bresnahan (BBB) scores. Three treatment groups were in the study: intrathecal-IgG, intrathecal-bovine serum albumin (BSA), and intrathecal saline-treated rats.

FIG. 2 illustrates that an overall treatment effect of IgG versus BSA and saline is found using the BBB scores. It was found that IgG treatment improves hindlimb motor recovery compared to BSA and saline controls. Of note here is that while a 2-point difference in BBB score is observed, the biological significance of this at the level between 7 and 10 on the BBB scale is impressive. Animals receiving a score of 7 will not have any stepping abilities or ability to bear weight at all, while an animal with a score of 9 can bear weight while standing and will attempt stepping with the hindpaws. 10 means that when stepping they are able to bear weight.

Figure 3A:
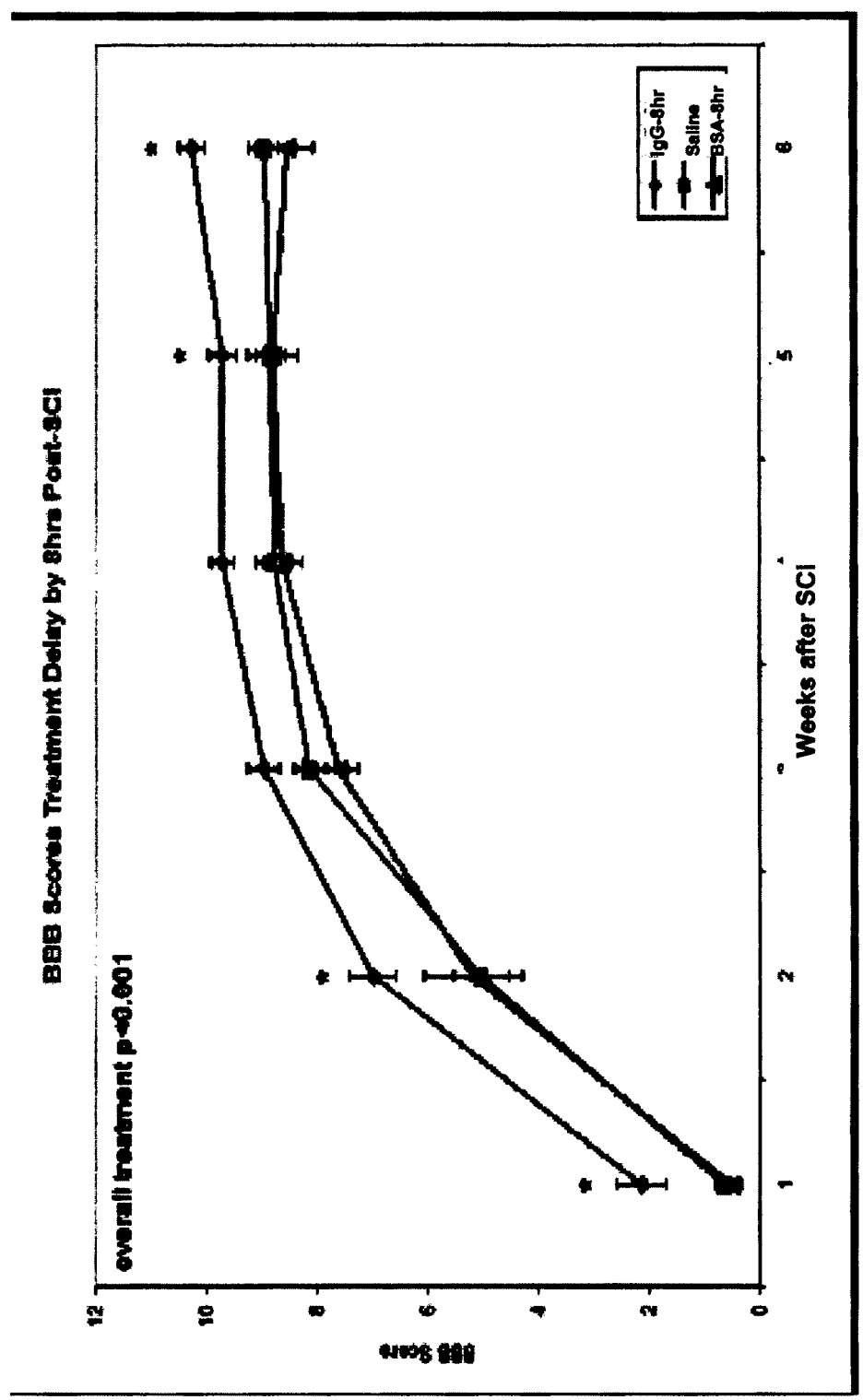
FIG. 3a illustrates that enhanced recovery of hindlimb function is maintained when intrathecal-IgG treatment is delayed by 8 hours post-SCI.
Figure 3B:
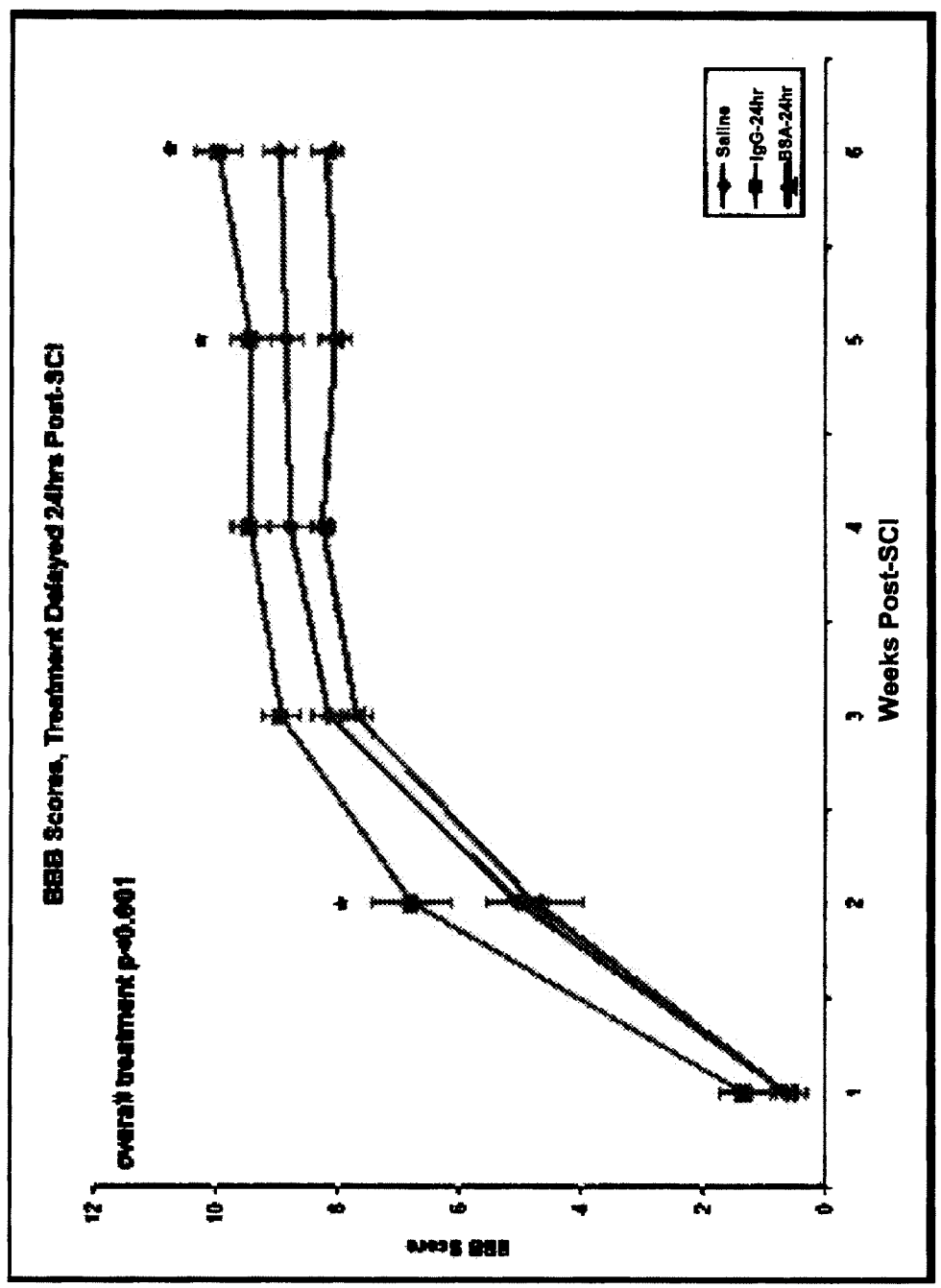
FIG. 3b illustrates that treatment delayed by 24 hours is also therapeutically beneficial.

Comparing IgG treatment delayed by 8 hours post-SCI with BSA treatment delayed by 8 hours and the saline controls, it is apparent that the enhanced recovery of hindlimb function is maintained (FIG. 3a). Furthermore, delaying treatment by 24 hours is also therapeutically beneficial (FIG. 3b). This is incredibly important because it indicates the clinically relevant nature of IgG treatment. Most therapeutic strategies being evaluated today do not come close to having maintained efficacy in a delayed administrative time window.

Having regard to the BBB scores to assess hindlimb motor recovery, IgG treatment is more beneficial than either BSA or saline treatment following SCI. The IgG treatment can be delayed by at least up to 24 hours with maintenance of a significantly improved motor recovery compared with BSA-treated and saline controls. Thus, intrathecal IgG treatment following SCI offers a clinically relevant therapeutic time window for administration with modest locomotor recovery benefits.

Figure 4:
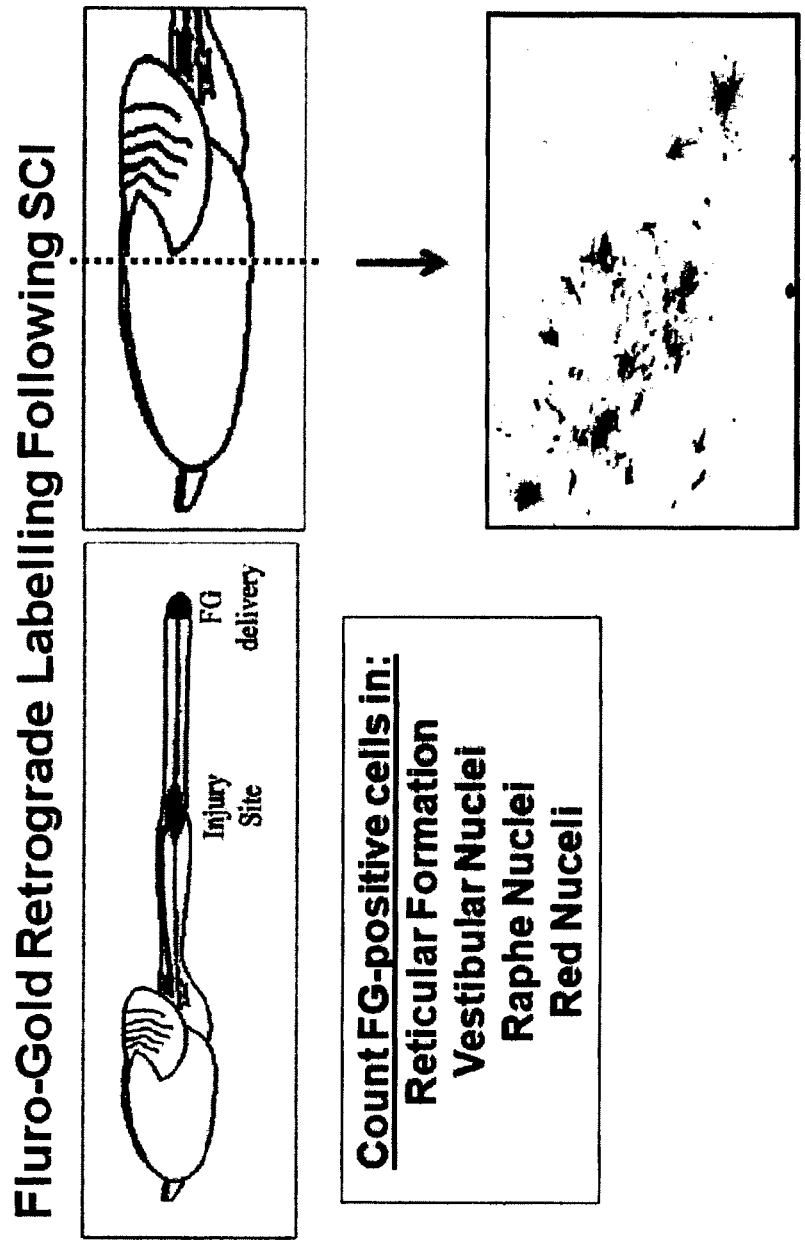
FIG. 4 illustrates Fluro-Gold (FG) retrograde labelling following SCI.

Fluro-Gold (FG) retrograde tracing was carried out following SCI, as noted above. What this evaluates is the ability of a treatment to preserve axons extending through and beyond the injury site. Any axons surviving the injury site will be able to pick up the inserted FG and will retrogradely transport the molecules to their cell bodies in the brain stem and mid-brain. By sectioning these areas of the brain and counting labelled neurons in specific brain regions, the treatment effects can be evaluated. Four brain areas (Reticular Formation, Vestibular Nuclei, Raphe Nuclei, and Red Nuclei) and the sum of all cells counted, were analysed as indicated in FIG. 4.

Figure 5:
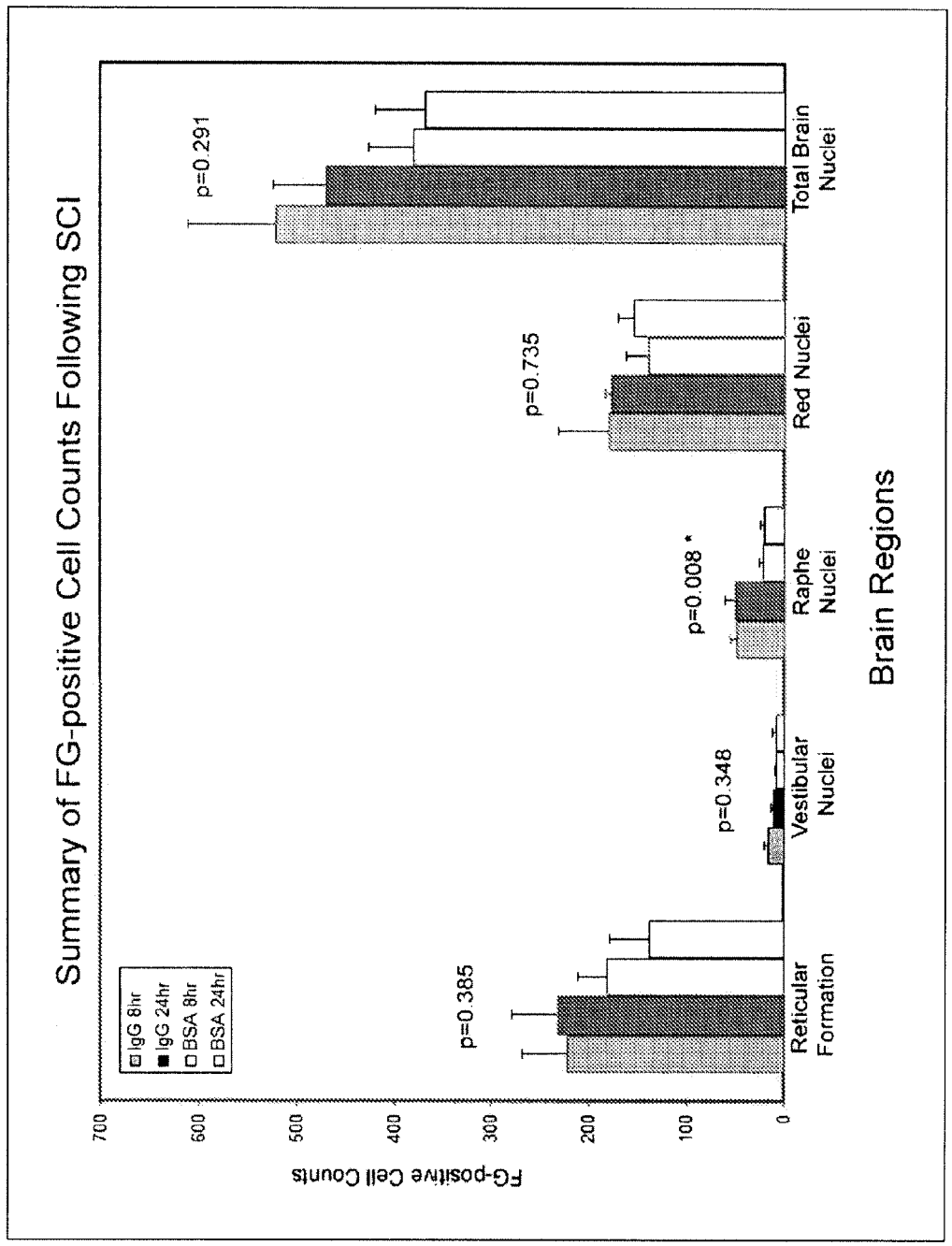
FIG. 5 illustrates a trend at all brain regions sampled for intrathecal-IgG treatment to have increased FG-positive cell counts, and therefore an increased preservation of axons extending through and beyond the injury site, and in the raphe nuclei this effect is statistically significant.

While there is a trend at all brain regions sampled for IgG treatment to have increased FG-positive cell counts, and therefore an increased preservation of axons extending through and beyond the injury site, it is in the raphe nuclei that this effect is statistically significant (FIG. 5).

Figure 6:
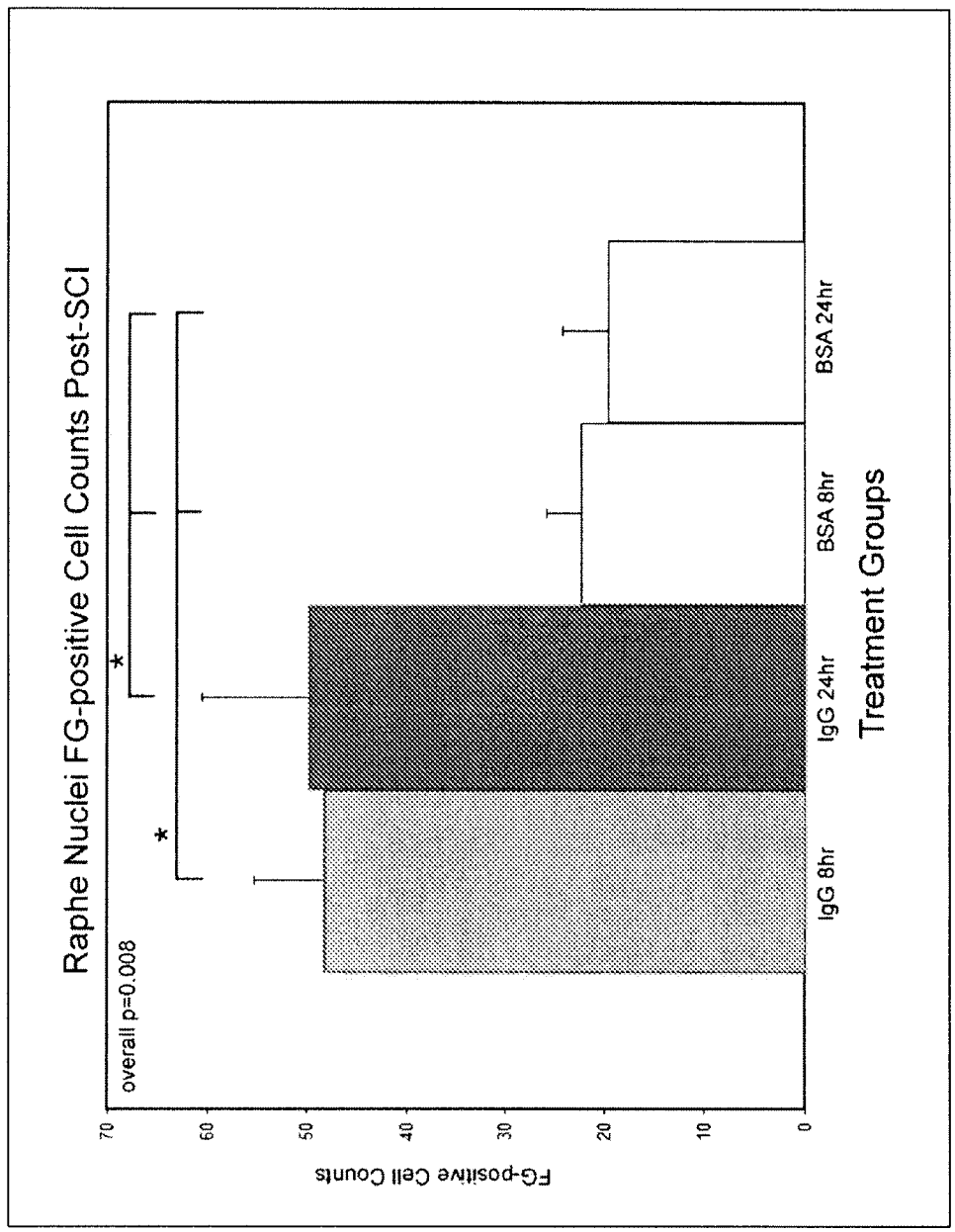
FIG. 6 illustrates that intrathecal-IgG treatment delayed by both 8 hours and 24 hours is able to prevent axonal degradation at the injury site as compared to both intrathecal-BSA treatments at 8 hours and 24 hours post-injury.

As illustrated in FIG. 6, IgG treatment delayed by both 8 hours and 24 hours is able to prevent axonal degradation at the injury site as compared to both BSA treatments at 8 hours and 24 hours post-injury. The preservation of Raphe nuclei-derived axons travelling through and beyond the injury site following SCI is improved for IgG treatment relative to BSA and saline-treated controls.

Figure 7:
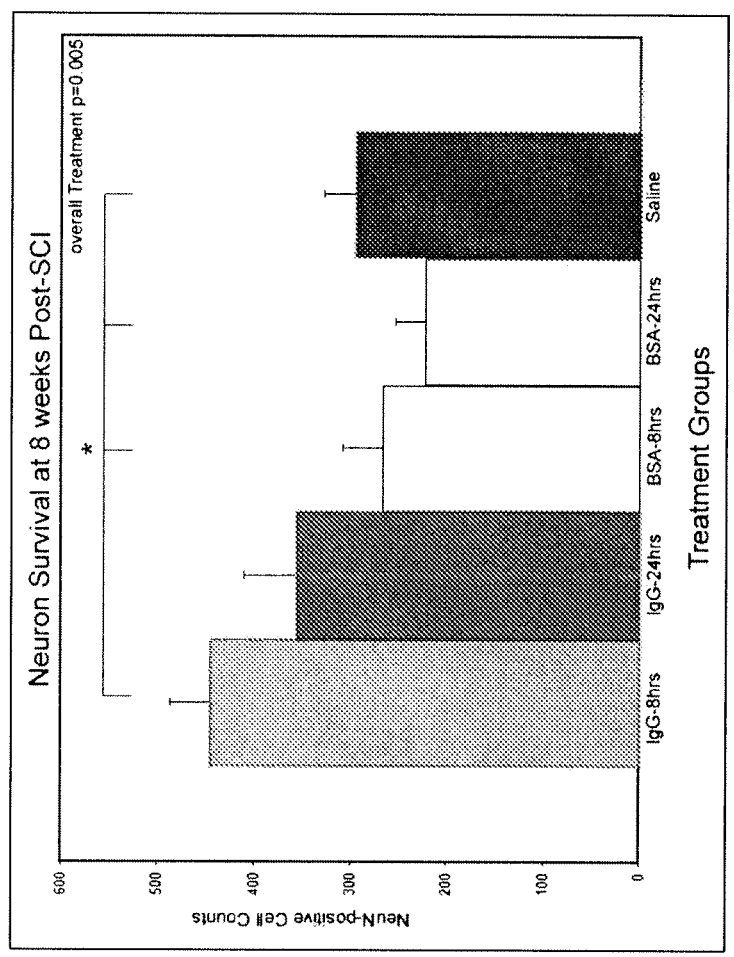
FIG. 7 illustrates the results of counting NeuN (a nuclear marker for neurons)-positive cells at approximately 700 μm rostral to the injury epicentre, at 8 weeks post-injury, which revealed that intrathecal-IgG treatment at 8 hours post-SCI was significantly able to enhance neuron survival when compared to BSA treated groups (both 8 hours and 24 hours) and saline controls.

Counting NeuN (a nuclear marker for neurons)-positive cells at approximately 700 µm rostral to the injury epicentre, at 8 weeks post-injury revealed that IgG treatment at 8 hours post-SCI was significantly able to enhance neuron survival when compared to BSA treated groups (both 8 hours and 24 hours) and saline controls (FIG. 7). This is important in that it gives merit to the observed behavioural results, especially when combined with the previously discussed FG data.

These results demonstrate that IgG treatment is effective for improving behavioural recovery and neuroanatomical preservation following SCI. The IgG treatment can be delivered in a clinically relevant time window, for example within 24 hours post-injury, with the 8 hour time point showing the most efficacious effects under the experimental conditions used herein.

A strong behavioural recovery effect is observed with IgG treatment following SCI, with supporting data to indicate a preservation of axons extending through and beyond the injury site, as well as an enhanced neuron survival in the tissue surrounding the injury site. It is postulated that IgG treatment offers beneficial immune modulating effects such as altering inflammatory cell activity and cytokine expression that contribute to its neuroprotective effects. Given the clinically valid time line of administration in this study and the current clinical use of IgG to treat various neuropathies, these findings show the potential for IgG administration to be a valid and translatable therapeutic strategy for SCI patients.

Figure 8:
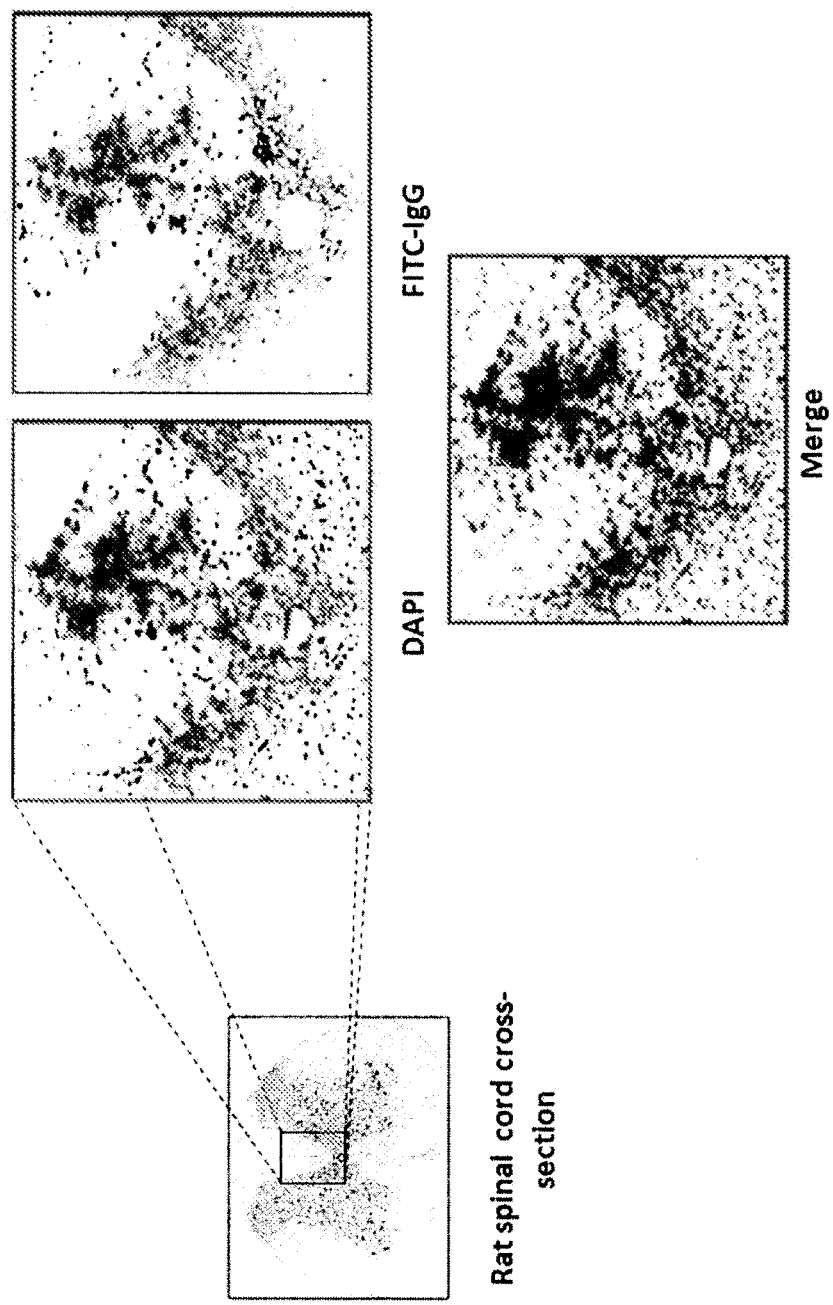
FIG. 8 illustrates IgG-FITC mainly localized in the dorsal column of the spinal cord. IgG conjugated to FITC (IgG-FITC) was delivered intrathecally to the spinal cord using catheter and mini-osmotic pump. Spinal cord was collected 3 days after SCI.

In order to determine if IgG is present at the injury epicenter following injection, IgG conjugated to the fluorescence molecule FITC (IgG-FITC) was delivered intrathecally right after SCI (SCI). Intrathecally delivered IgG-FITC mainly localized in the dorsal column of the spinal cord at 3 days post SCI (FIG. 8).

The biological effect of IgG was tested by assaying for the level of neutrophils at the injury epicenter following SCI. Neutrophil infiltration following SCI is thought to increase the magnitude of the secondary injury process and lead to poor functional recovery. Treatments that aimed at blocking neutrophil infiltration have been shown to improve functional recovery following SCI in animal and human.

Figure 10:
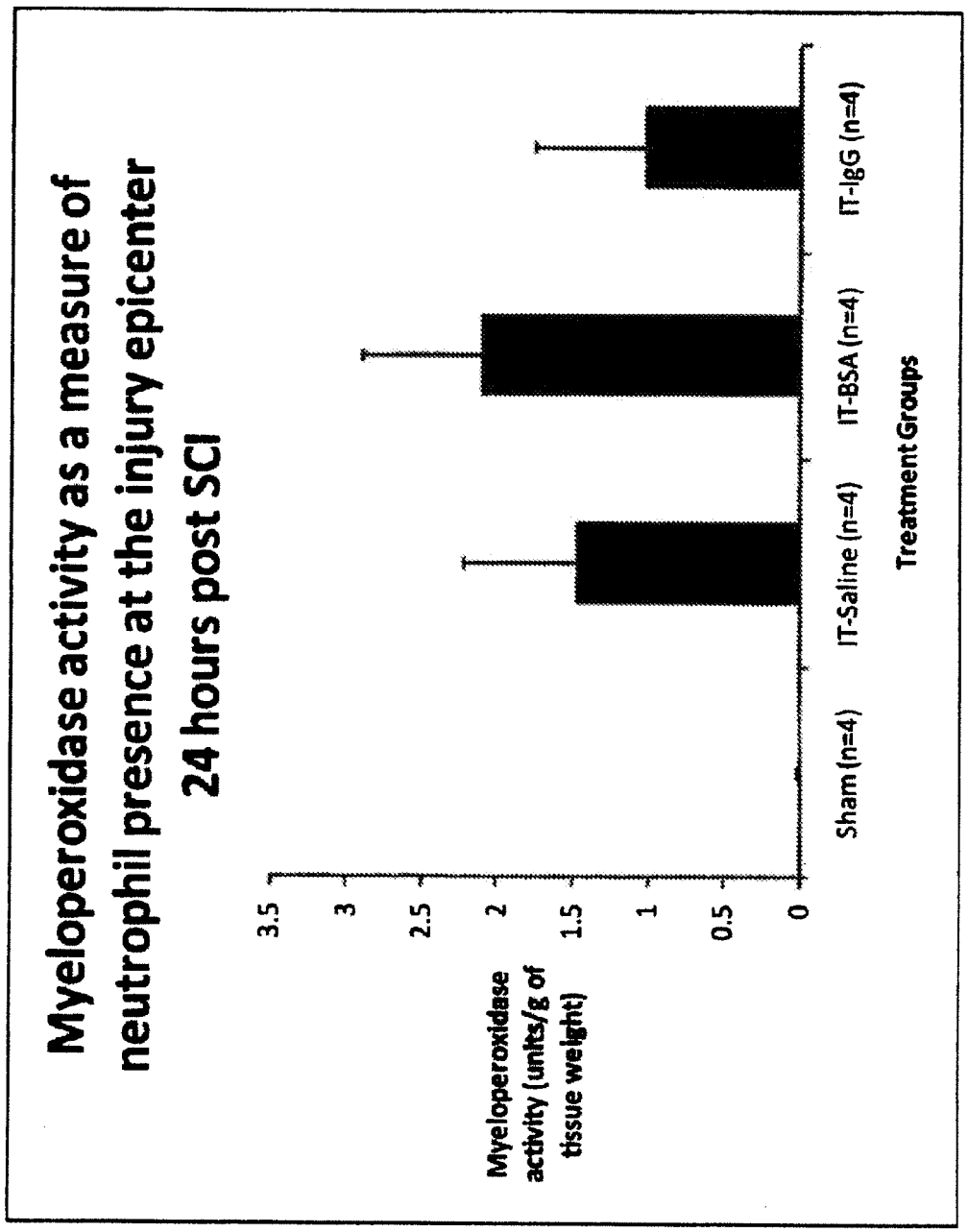
FIG. 10 illustrates neutrophil presence measured by myeloperoxidase at the injury epicenter 24 hours post-SCI. IgG or saline were treated intrathecally (IT) by mini-osmotic pumps at 8 hours following SCI. Although there is a trend toward less neutrophil presence in the IgG treatment groups, the difference between saline vs. IgG is not statistically significant at this time point.

IgG was delivered intrathecally via miniosmotic pumps and catheters at 8 hours post-SCI. Myeloperoxidase activity assay (MPO) was used as a measure of neutrophil infiltration at the injury epicenter at 24 hrs post-SCI. As shown in FIG. 10, although a trend toward lower level of neutrophils was observed in animals that received Intrathecal-IgG, the difference was not statistically significant when compared to saline treated animals.

EXAMPLE II

Using a moderately severe clip compression injury model in adult female Wistar rats, the objective of this study was to evaluate the inflammatory and neuroprotective effects of intravenous delivery of IgG following SCI.

The clip compression model of SCI was used in these experiments, with adult female Wistar rats receiving a 35 g compression injury using a calibrated aneurysm clip (with 35 g of closing force) at the level of C7-T1 vertebrae (FIG. 1).

IgG was injected at a single dose of 0.4 g/kg into the rat's tail-vein 15 minutes post-SCI. Intravenous treatment of IgG is less invasive and can be administered independent of surgical intervention. Therefore, the treatment of IgG intravenously at 15 minutes post-SCI could be relatively clinical relevant.

Figure 9:
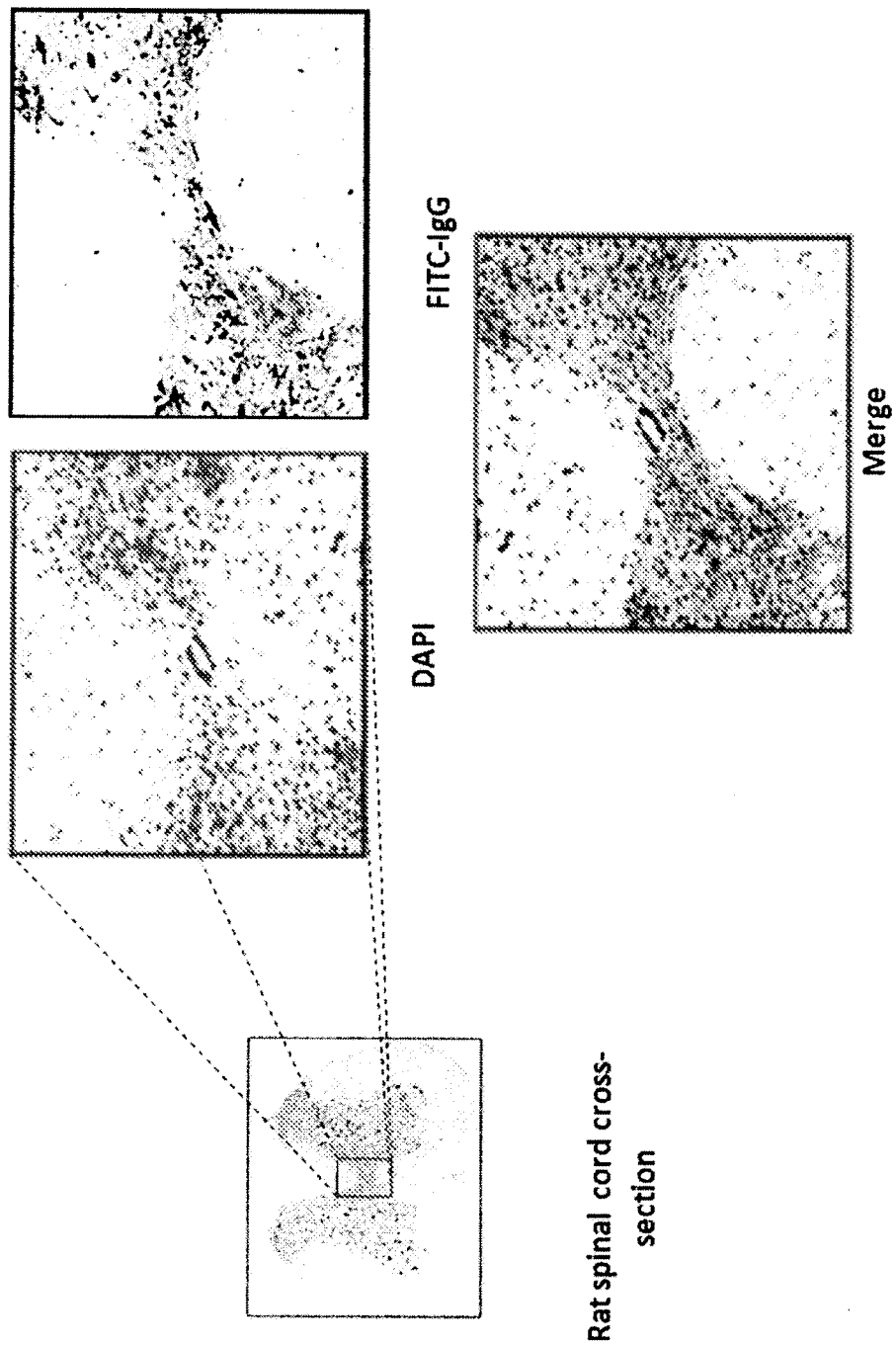
FIG. 9 illustrates IgG-FITC mainly localized in the grey-matter. IgG conjugated to FITC (IgG-FITC) was injected intravenously via tail vein. Spinal cord was collected 2 days after SCI.

As a proof-of-concept, IgG conjugated to FITC was injected intravenously right after injury. Intravenously delivered IgG-FITC could be observed in the grey and white matter at 2 days post-SCI, with the highest density in the grey matter (FIG. 9).

Figure 11:
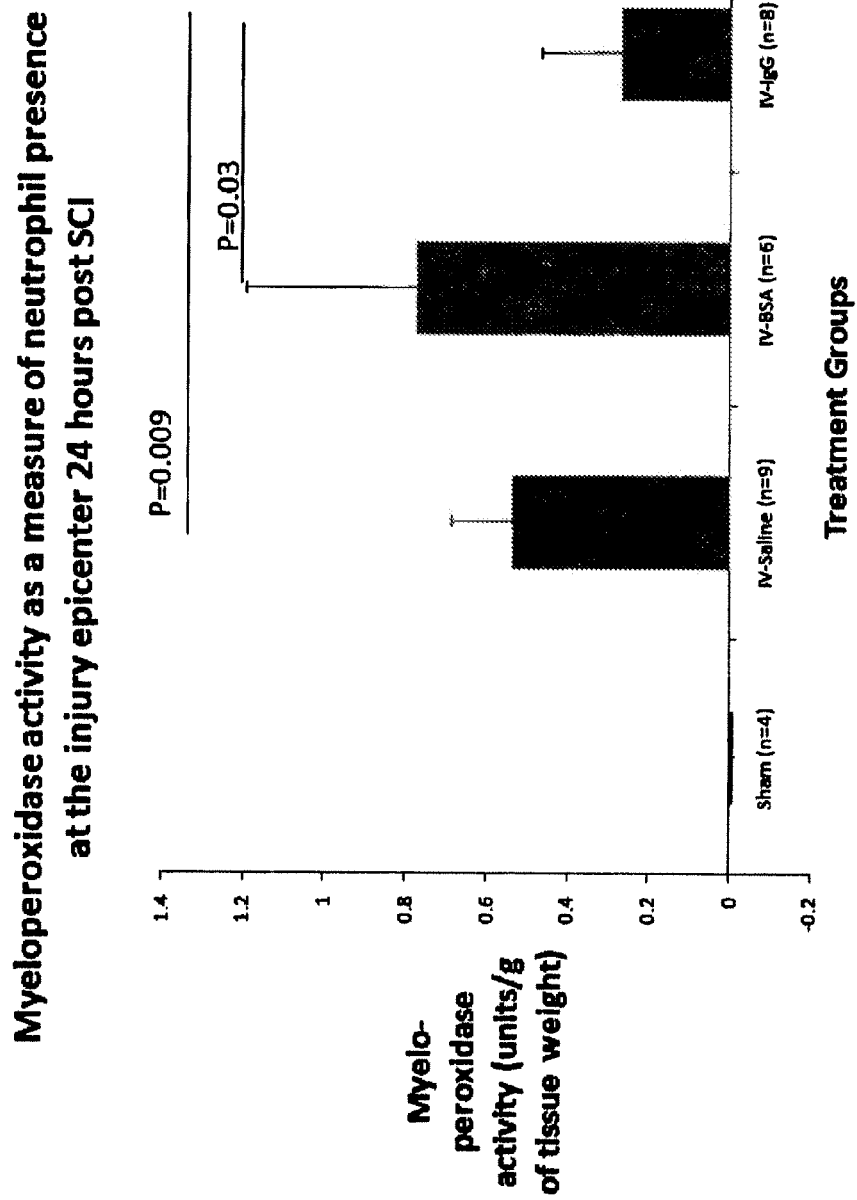
FIG. 11 illustrates neutrophil presence measured by myeloperoxidase at the injury epicenter 24 hours post SCI. IgG, BSA, and saline was injected intravenously 15 minutes following SCI. The differences in neutrophils presence between IgG vs. Saline or IgG vs. BSA treated rats are statistically significant (p=0.009 and p=0.0, respectively)

In order to investigate whether intravenous-IgG attenuates neutrophil infiltration following SCI, IgG, saline, or BSA was injected intravenously at 15 minutes post-SCI. Animals were sacrificed at 24 hours post-SCI for analysis. The difference in the level of neutrophil presence at the injury epicenter was statistically significant (p=0.009) (FIG. 11).

Figure 12:
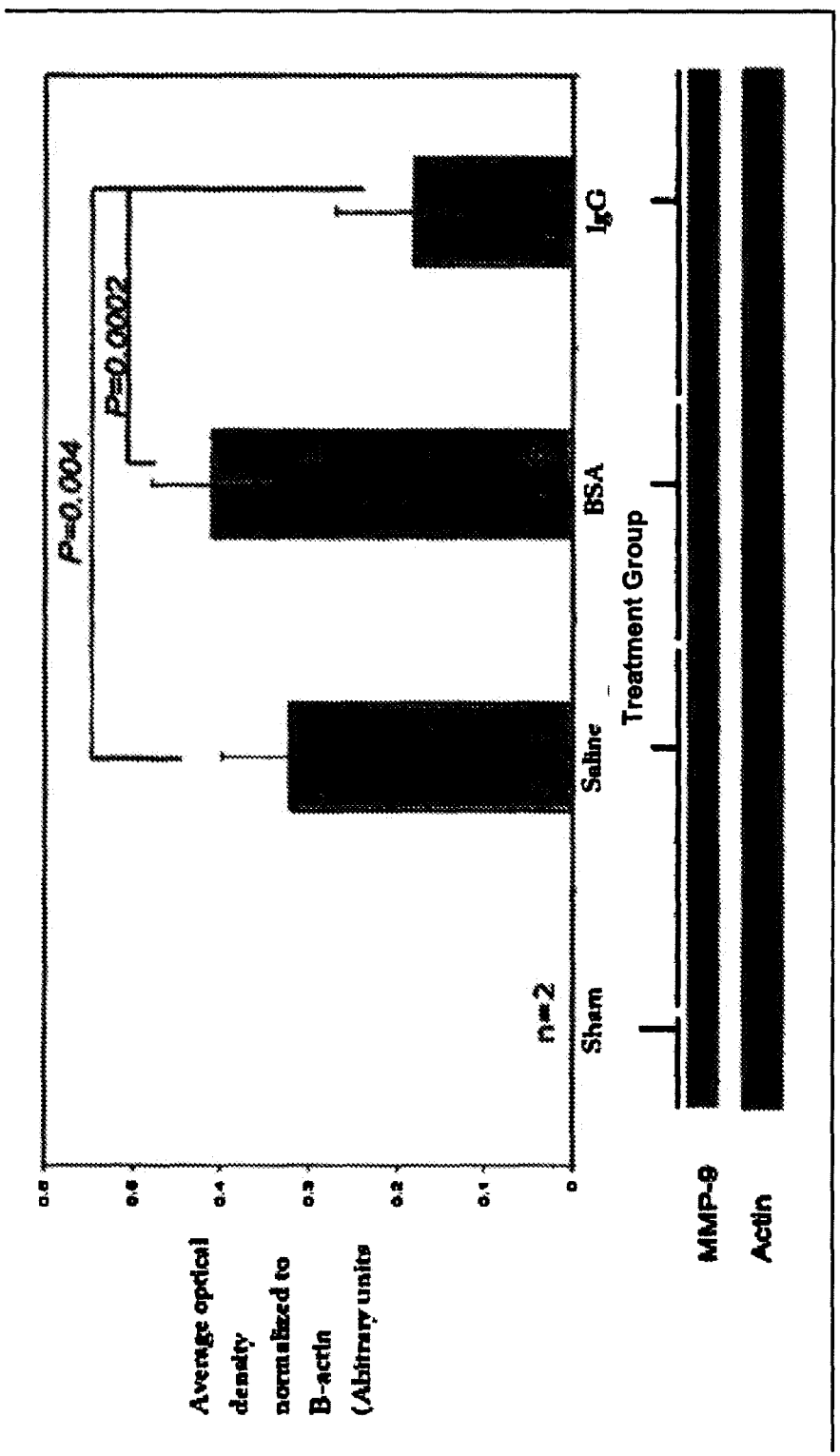
FIG. 12 illustrates the production of matrix-metalloproteinase-9 (MMP-9) assessed by western blot. One-way ANOVA analysis showed that there is a treatment effect (P<0.05). Post-hoc t-test showed that there is significantly less MMP-9 produced in animals that received intravenous-IgG compared to saline and BSA-treated animals (p=0.004 and p=0.0002, respectively).

In addition, western blot was used to assess the level of matrix-metalloproteinase-9 (MMP-9) at the injury epicenter at 24 hours post-SCI. The up-regulation of MMP-9 after SCI is implicated to result in poor outcome and functional recovery. MMP-9 was significantly reduced in animals that received intravenous IgG (FIG. 12). This evidence is supportive of the MPO data since neutrophil is a significant source of MMP-9. The data overall provide a strong evidence that IgG has a biological effect following SCI. In addition, IgG can be use intravenously to treat SCI.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

The embodiments of the invention described above are intended to be exemplary only. The scope of the invention is therefore intended to be limited solely by the scope of the appended claims.

The references cited throughout the application and in the list provided below are hereby incorporated by reference.

References

1. Christopher and Dana Reeve Foundation. Prevalence of Paralysis. 2009 July Cited. Available at:
2. Spinal Cord Injury Information Network. Spinal Cord Injury Facts and Figures at a Glance 2009. 2009 July cited. Available at:
3. Young, W. *Secondary Injury Mechanisms in Acute Spinal Cord Injury*. J. Emerg Med., 1993. 11: p. 13-22.
4. Blight, A. *Delayed demyelination, macrophage invasion: a candidate for "secondary" cell damage in spinal cord injury*. Cent Nery Syst Trauma, 1985. 2: p. 299-315.
5. Tator, C., Fehlings, M. *Review of the secondary injury theory of acute spinal cord trauma with emphasis on vascular mechanisms*. J. Neurosurg., 1991. 75: p. 15-26.
6. Kwon, B., Tetzlaff, W., Grauer, J., Beiner, J., Vaccaro, R. *Pathophysiology and pharmacologic treatment of acute spinal cord injury*. Spine J., 2004. 4: p. 451-64.
7. Profyris, C., Cheema, S., Zang, D W., Azari, M., Boyle, K., Petratos, S. *Degenerative and regenerative mechanisms governing spinal cord injury*. Neurobiology of Disease, 2004. 15: p. 415-436.
8. Fleming, J., Norenberg, M., Ramsay, D., Dekaban, G., Marcillo, A., Saenz, A., Pasquale-Styles, M., Dietrich, W. *The cellular inflammatory response in human spinal cords after injury*. Brain, 2006. 129: p. 3249-3269.
9. Hausmann, O. *Post-traumatic inflammation following spinal cord injury*. Spinal Cord, 2003. 41: p. 369-378.
10. Popovich, P., Wei, P., Stokes, B., *The cellular inflammatory response after spinal cord injury in Sprague-Dawley and Lewis rats*. J. Comp. Neurol., 1997. 377 p. 443-464.
11. Sroga, J., Jones, T., Kigerl, K., Mcgaughy, V., Popovich, P. *Rats and mice exhibit distinct inflammatory reactions after spinal cord injury*. J. Comp. Neurol., 2003. 462: p. 223-240.
12. Donnelly, D., Popovich, P. *Inflammation and its role in neuroprotection, axonal regeneration and function recovery after spinal cord injury*. Experimental Neurology, 2007. 209: p. 378-388.
13. Cassatella, M. *The production of cytokines by polymorphonuclear neutrophils*. Immunol. Today, 1995. 16: p. 21-26.
14. Clark, R., Kochanek, P., Schwarz, M., Schiding, J., Turner, D., Chen, M., Carlos, T., Watkins, C., *Inducible nitric oxide synthase expression in the cerebrovascular smooth muscle and neutrophils after traumatic brain injury in immature rats*. Pediatr. Res., 1996. 39: p. 784-790.
15. MacMicking, J., Xie, Q W., Nathan, C. *Nitric oxide and macrophage function*. Annu. Rev. Immunol., 1997. 15: p. 323-350.
16. Beckman J., Beckman, T., Chen, J., Marshall, P. A., Freeman B. A. *Apparent hydroxyl radical production by peroxynitrite: implications for endothelial injury from nitric oxide and superoxide*. PNAS, 1990. 87: p. 1620-1624.
17. Horn, K., Busch, S., Hawthorne, A L., van Rooijen, N., Silver, J. *Another barrier to regeneration in the CNS: activated macrophages induce extensive retraction of dystrophic axons through direct physical interactions*. J. Neurosci., 2008. 28: p. 9330-41.
18. Kansas, G. *Selectins and their ligands: current concepts and controversies*. Blood, 1996. 88: p. 3259-3287.
19. Lee, Y., Shih, K., Bao, P., Ghirnikar, R., Eng, L. *Cytokine chemokine expresssion in contused rat spinal cord*. Neurochem. Int., 2000b. 36: p. 417-425.
20. McTigue, D., Tani, M., Krivacic, K., et al. *Selective chemokine mRNA accumulation in the rat spinal cord after contusion injury*. J. Neurosci. Res., 1998. 53: p. 368-376.
21. Schnell, L., Fearn, S., Klassen, H., Schwab, M., Perry, V. *Acute inflammatory responses to mechanical lesions in the CNS: differences between brain and spinal cord*. Eur. J. Neurosci, 1999. 11: p. 3648-3658.
22. Young, W. *Methylprednisolone and spinal cord injury*. J. Neurosurg., 2002. 96: p. 141-142.
23. Popovich, P., Guan, Z., Wei, P., Huitinga, I., van Rooijen, N., Stokes B. *Depletion of hematogenous macrophages promotes partial hindlimb recovery and neuroanatomical repair after experimental spinal cord injury*. Experimental Neurology, 1999. 158: p. 351-365.
24. Noble, L., Donovan, F., Igarashi, T., Goussev, S., Werb, Z. *Matrix metalloproteinases limit functional recovery after spinal cord injury by modulation of early vascular events*. J. Neurosci., 2002. 22: p. 7526-7535.

25. Taoka, Y., Okajima, K., Uchiba, M., Murakami, K., Kushimoto, S., Johno, M., et al. *Role of neutrophils in spinal cord injury in the rat. Neuroscience*. Neuroscience, 1997. 79: p. 1177-82.
26. Ditor, D., Bao, F., Chen, Y., Dekaban, G., Weaver L. *A therapeutic time window for anti-CD11d monoclonal antibody treatment yielding reduced secondary tissue damage and enhanced behavioral recovery following severe spinal cord injury*. J. Neurosurg. Spine, 2006. 5: p. 343-352.
27. Gris, D., Marsh, D., Oatway, M., Chen, Y., Hamilton, E., Dekaban G., Weaver, L., *Transient blockade of the CD11d/CD18 integrin reduces secondary damage after spinal cord injury, improving sensory, autonomic, and motor function*. J. Neurosci., 2004. 24: p. 4043-4051.
28. Prasad N, Papoff G, Zeuner A, et al: Therapeutic preparations of normal polyspecific IgG (IVIg) induce apoptosis in human lymphocytes and monocytes: a novel mechanism of action of IVIg involving the Fas apoptotic pathway. J Immunol. 161: 3781-3790, 1998.
29. Stephan von Gunten, et al: Immunologic and functional evidence for anti-Siglec-9 autoantibodies in intravenous immunoglobulin preparations. Blood, 109: 4255-4258, 2006.
30. Shapiro S, Shoenfeld Y, Gilburd B, Sobel E, Lahat N: Intravenous Gamma Globulin Inhibits the Production of Matrix Metalloperoteinase-9 in Macrophages. Cancer, 95: 2032-2037, 2002.
31. Basta M, et al: F(ab)'2-mediated neutralization of C3a and C5a anaphylatoxins: a novel effector function of immunoglobulins. Nat. Med. 9: 431-438, 2003.
32. Marder S, Chenoweth D, Goldstein I, Perez H: Chemotactic responses of human peripheral blood monocytes to the complement-derived peptides C5a and C5a Des Arg. J. Immunol. 134: 3325-3331, 1985.
33. Schmidt R, Gessner J: Fc receptors and their interaction with complement in autoimmunity. Immunology Letters. 100: 56-57, 2005.
34. Anthony R, Wermelling F, Karlsson M, Ravetch J: Identification of a receptor required for the anti-inflammatory activity of IVIG. PNAS. 105: 19571-19578, 2008.

The invention claimed is:

1. A method for promoting locomotor recovery or reducing locomotor damage following spinal cord injury comprising the step of administering to a spinal cord injury victim an effective amount of immunoglobulin G (IgG).

2. The method of claim 1, wherein the spinal cord injury victim is human and the IgG is IgG from pooled human serum.

3. The method of claim 2, wherein the effective amount of IgG is at least partially administered within 24 hours of spinal cord injury.

4. The method of claim 3, wherein the effective amount of IgG is at least partially administered within 12 hours of spinal cord injury.

5. The method of claim 3, wherein the effective amount of IgG is administered in a single dose.

6. The method of claim 3, wherein the effective amount of IgG is administered in multiple doses.

* * * * *